United States Patent
Nampoothiri K. et al.

(10) Patent No.: US 6,949,374 B2
(45) Date of Patent: Sep. 27, 2005

(54) **FADD15 GENE OF *CORYNEBACTERIUM GLUTAMICUM*, ENCODING AN ACYL-COA SYNTHASE POLYPEPTIDE**

(75) Inventors: Madhavan Nampoothiri K., Kerala (IN); Bettina Möckel, Düsseldorf (DE); Walter Pfefferle, Halle (DE); Lothar Eggeling, Jülich (DE); Hermann Sahm, Jülich (DE)

(73) Assignee: Degussa AG, Düsseldorf (DE)

( * ) Notice: Subject to any disclaimer, the term of this patent is extended or adjusted under 35 U.S.C. 154(b) by 499 days.

(21) Appl. No.: 09/855,750

(22) Filed: May 16, 2001

(65) Prior Publication Data

US 2002/0042107 A1 Apr. 11, 2002

Related U.S. Application Data

(63) Continuation-in-part of application No. 09/577,848, filed on May 25, 2000, now abandoned.

(30) Foreign Application Priority Data

May 4, 2000 (DE) .......................................... 100 21 831

(51) Int. Cl.[7] ............................ C12N 1/20; C07H 21/04
(52) U.S. Cl. .................. 435/252.3; 536/23.1; 536/23.2; 536/23.7; 536/24.32; 536/24.33; 435/320.1; 435/252.32
(58) Field of Search ................. 435/193, 252.3, 435/320.1, 252.32; 536/23.7, 23.2, 23.1, 24.32, 24.33

(56) References Cited

U.S. PATENT DOCUMENTS 6,696,561 B1 * 2/2004 Pompejus et al. ......... 536/23.7

FOREIGN PATENT DOCUMENTS

| EP | 1 108 790 A2 | 6/2001 |
|---|---|---|
| WO | WO 99/18228 | 4/1999 |

OTHER PUBLICATIONS

Fujino et al. (1996) J Biol Chem 271(28):16748–16752.*
Broun et al. (1998) Science 282:1315–1317.*
Bernhard J. Eikmanns., et al. "Molecular aspects of lysine, threonine, and isoleucine biosynthesis in *Corynebacterium glutamicum*," Antonic van Leeuwenhoek vol. 64, 1993, pp. 145–163.

* cited by examiner

*Primary Examiner*—David J. Steadman
(74) *Attorney, Agent, or Firm*—Smith Gambrell & Russell

(57) ABSTRACT

The invention relates to a genetically modified coryneform bacterium, the fadD15 gene of which is amplified, and an isolated polynucleotide which codes for acyl-CoA synthase from coryneform bacteria, and also a method for the fermentative preparation of L-amino acids with amplification of the fadD15 gene in the bacteria and the use of the polynucleotide as a primer or hybridization probe.

17 Claims, 2 Drawing Sheets

Figure 1: Plasmid pJC1fadD15
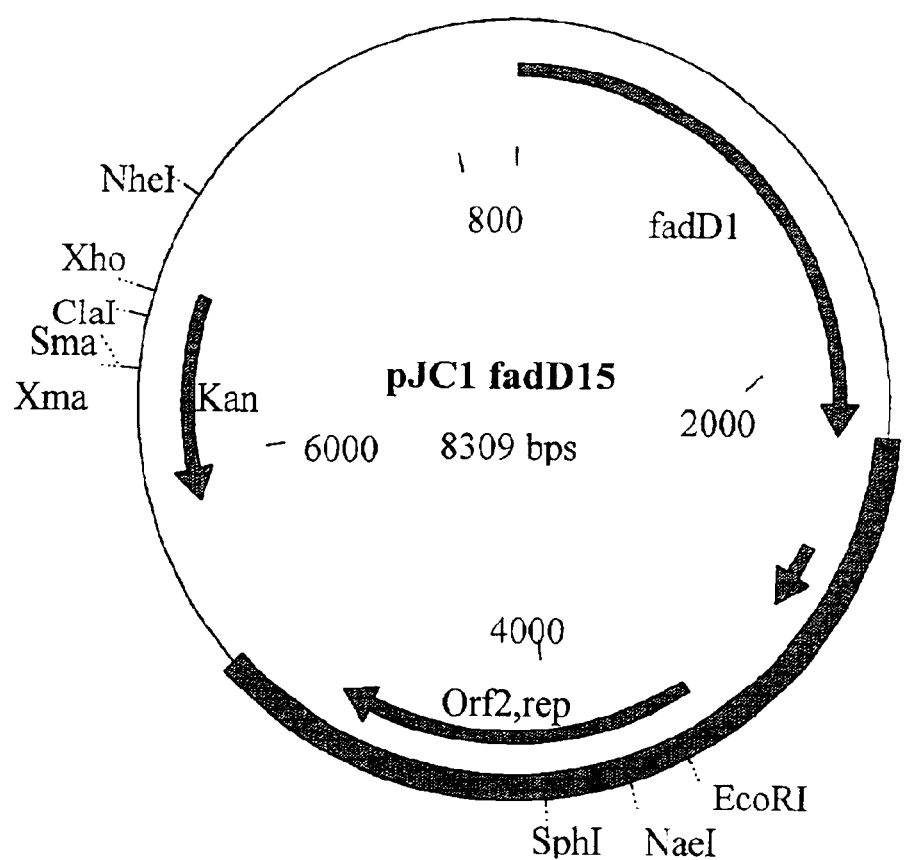

Figure 2: Growth growth of *C. glutamicum* ATCC 13032 (◆) and ATCC 13032/pJC1fadD15 (■) at 40°C.
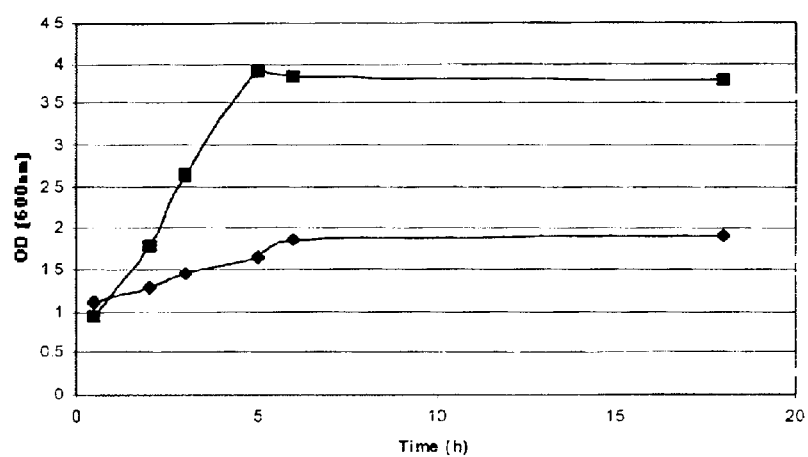

SEQUENCE LISTING

```
<160> NUMBER OF SEQ ID NOS: 4

<210> SEQ ID NO 1
<211> LENGTH: 2300
<212> TYPE: DNA
<213> ORGANISM: Corynebacterium glutamicum
<220> FEATURE:
<221> NAME/KEY: CDS
<222> LOCATION: (247)..(2103)
<223> OTHER INFORMATION:
<221> NAME/KEY: -10_signal
<222> LOCATION: (95)..(100)
<223> OTHER INFORMATION:
<221> NAME/KEY: -35_signal
<222> LOCATION: (72)..(78)
<223> OTHER INFORMATION:
<221> NAME/KEY: RBS
<222> LOCATION: (188)..(195)
<223> OTHER INFORMATION:

<400> SEQUENCE: 1
ttatgccact aatagcgtgt gggcacagca tatttgtagc gtgagggtaa gtttgttaga      60
aaatacatct tttggattgg gctttggggt ggcttttata caccctgatt ggtgcagata     120
taagaagtta ttgacacact gaatacatag agaaaaattc catgtggtta aagatatgcc     180
taaagatctg accaaaaacg tgactaaaga cgtgacgaca caagtacagc caaattaaag     240 gaaagg ttg aat ttg acc atg act tca cct aat acc ctg cag gaa tac        288
       Leu Asn Leu Thr Met Thr Ser Pro Asn Thr Leu Gln Glu Tyr
         1               5                  10 act gaa cct gcc aag tac acc atc gga gaa tct gaa acc tgc ctg acc      336
Thr Glu Pro Ala Lys Tyr Thr Ile Gly Glu Ser Glu Thr Cys Leu Thr
 15                  20                  25                  30 gcc ctt cta gat cag att aag act cga cct tac gga gtt ttg ttc agc      384
Ala Leu Leu Asp Gln Ile Lys Thr Arg Pro Tyr Gly Val Leu Phe Ser
                 35                  40                  45 aag cct gcc aac tat gag tgg gtg aat gta act gcc aaa gaa ttt cag      432
Lys Pro Ala Asn Tyr Glu Trp Val Asn Val Thr Ala Lys Glu Phe Gln
             50                  55                  60 gac gag gtt ttt gcg gtt gca aaa gga att att tca gtc ggc gta gag      480
Asp Glu Val Phe Ala Val Ala Lys Gly Ile Ile Ser Val Gly Val Glu
 65                  70                  75 cag gga gac cgt gtc gcg ctg ctg tcc aat act cgc tat gag tgg gct      528
Gln Gly Asp Arg Val Ala Leu Leu Ser Asn Thr Arg Tyr Glu Trp Ala
 80                  85                  90 gtg ctt gat ttc gct atc tgg gcc gct ggc gca gtg agc gtg cct atc      576
Val Leu Asp Phe Ala Ile Trp Ala Ala Gly Ala Val Ser Val Pro Ile
 95                 100                 105                 110 tac agc tcc tct tca ctg tcc caa att gag tgg atc att gag gat tcc      624
```

```
Tyr Ser Ser Ser Ser Leu Ser Gln Ile Glu Trp Ile Ile Glu Asp Ser
            115                 120                 125 ggc gct gtt ttg gcc att acc gaa acc cct gat cat acc gac ttg atg      672
Gly Ala Val Leu Ala Ile Thr Glu Thr Pro Asp His Thr Asp Leu Met
            130                 135                 140 aag aac ctg gtc atc ggt gaa gac gga act cca gcg att aag ggt tca      720
Lys Asn Leu Val Ile Gly Glu Asp Gly Thr Pro Ala Ile Lys Gly Ser
            145                 150                 155 cct tcc aag ctg cgc cgc att cta gag atc aac tct tcg gcg ttg gag      768
Pro Ser Lys Leu Arg Arg Ile Leu Glu Ile Asn Ser Ser Ala Leu Glu
        160                 165                 170 acc ttg aag ttt gag ggc cgc gag ctt tct gat gag ctg gtg tgg gaa      816
Thr Leu Lys Phe Glu Gly Arg Glu Leu Ser Asp Glu Leu Val Trp Glu
175                 180                 185                 190 cgc att cat gca acc aag gcc gct gac ctg gcg tct ttg gtg tac acc      864
Arg Ile His Ala Thr Lys Ala Ala Asp Leu Ala Ser Leu Val Tyr Thr
                195                 200                 205 tct ggc aca act ggt agg ccg aag ggc tgc gag ttg tcc cac tac cac      912
Ser Gly Thr Thr Gly Arg Pro Lys Gly Cys Glu Leu Ser His Tyr His
            210                 215                 220 tgg ttg gct gag gtc cga gcg ctg atc acc aat gac atc gga gcg atc      960
Trp Leu Ala Glu Val Arg Ala Leu Ile Thr Asn Asp Ile Gly Ala Ile
            225                 230                 235 gcg atg cca ggt tca agg ttg ctc acc ttc ctt cct ttg gcg cac gtt     1008
Ala Met Pro Gly Ser Arg Leu Leu Thr Phe Leu Pro Leu Ala His Val
            240                 245                 250 ctt gct cgc gca gtg cac ttg gcc ttc gct gtc acc ggt gca acc cag     1056
Leu Ala Arg Ala Val His Leu Ala Phe Ala Val Thr Gly Ala Thr Gln
255                 260                 265                 270 tcc cac tgg tct gat ttc agc acc ctt act ttg gaa ctg cag cgt tcc     1104
Ser His Trp Ser Asp Phe Ser Thr Leu Thr Leu Glu Leu Gln Arg Ser
                275                 280                 285 cgc ccg aac ctg att ttg ggt gtt cca cgc gtg ttt gaa aag gtc cgc     1152
Arg Pro Asn Leu Ile Leu Gly Val Pro Arg Val Phe Glu Lys Val Arg
            290                 295                 300 aac gcc gct gct gct aat gct gct gac ggt ggc gca atc aag cgc atc     1200
Asn Ala Ala Ala Ala Asn Ala Ala Asp Gly Gly Ala Ile Lys Arg Ile
            305                 310                 315 atg ttt gag cgt gcc gaa aag gcg gcc att gaa tac tcc atg gct ctt     1248
Met Phe Glu Arg Ala Glu Lys Ala Ala Ile Glu Tyr Ser Met Ala Leu
            320                 325                 330 gat act gca gaa ggc cca agc aag tcc cag gtt atg gca cat aaa gcg     1296
Asp Thr Ala Glu Gly Pro Ser Lys Ser Gln Val Met Ala His Lys Ala
335                 340                 345                 350 ttt gac aag ctg gtg tac tcc aag atc cgt gca gct gtc ggt ggc gat     1344
Phe Asp Lys Leu Val Tyr Ser Lys Ile Arg Ala Ala Val Gly Gly Asp
                355                 360                 365 gtg cag tac gcc atc acc ggt ggt tca gcg atg ggg cag gag ctg ctg     1392
Val Gln Tyr Ala Ile Thr Gly Gly Ser Ala Met Gly Gln Glu Leu Leu
            370                 375                 380 cac ttc ttc cgc ggt gtg ggc atg acc atc tac gaa ggt tat ggt ctg     1440
His Phe Phe Arg Gly Val Gly Met Thr Ile Tyr Glu Gly Tyr Gly Leu
            385                 390                 395 acg gaa tct gcg gct gct gca gcg gtg gac ttc act gat caa aag atc     1488
Thr Glu Ser Ala Ala Ala Ala Val Asp Phe Thr Asp Gln Lys Ile
            400                 405                 410 ggc act gtg ggt aag ccg atg ggt ggc atg acc atc aag atc aat gaa     1536
Gly Thr Val Gly Lys Pro Met Gly Gly Met Thr Ile Lys Ile Asn Glu
415                 420                 425                 430
```

| | | | | | | | | | | | | | | | | |
|---|---|---|---|---|---|---|---|---|---|---|---|---|---|---|---|---|
|gat|ggc|gaa|atc|atg|cta|aaa|ggc|gag|atg|ttg|ttc|cag|gga|tat|tgg|1584|
|Asp|Gly|Glu|Ile|Met|Leu|Lys|Gly|Glu|Met|Leu|Phe|Gln|Gly|Tyr|Trp| |
| | | | |435| | | | |440| | | | |445| | |

| | | | | | | | | | | | | | | | | |
|---|---|---|---|---|---|---|---|---|---|---|---|---|---|---|---|---|
|aac|aac|cca|gaa|gcc|aca|gca|gaa|gcc|ctc|cac|gac|ggt|tgg|ttc|aac|1632|
|Asn|Asn|Pro|Glu|Ala|Thr|Ala|Glu|Ala|Leu|His|Asp|Gly|Trp|Phe|Asn| |
| | | |450| | | | |455| | | | |460| | | |

| | | | | | | | | | | | | | | | | |
|---|---|---|---|---|---|---|---|---|---|---|---|---|---|---|---|---|
|acc|ggc|gat|ctg|ggt|gag|ctg|ttg|gag|tct|gga|cac|ctg|gtg|atc|acc|1680|
|Thr|Gly|Asp|Leu|Gly|Glu|Leu|Leu|Glu|Ser|Gly|His|Leu|Val|Ile|Thr| |
| | |465| | | | |470| | | | |475| | | | |

| | | | | | | | | | | | | | | | | |
|---|---|---|---|---|---|---|---|---|---|---|---|---|---|---|---|---|
|gga|cgt|aag|aaa|gat|ctg|atc|gtg|acc|gcg|ggc|ggc|aag|aac|gtt|tcc|1728|
|Gly|Arg|Lys|Lys|Asp|Leu|Ile|Val|Thr|Ala|Gly|Gly|Lys|Asn|Val|Ser| |
| |480| | | | |485| | | | |490| | | | | |

| | | | | | | | | | | | | | | | | |
|---|---|---|---|---|---|---|---|---|---|---|---|---|---|---|---|---|
|cca|gga|ccc|atg|gaa|gac|atc|atc|cgc|gca|cac|cca|ctg|gtc|agc|cag|1776|
|Pro|Gly|Pro|Met|Glu|Asp|Ile|Ile|Arg|Ala|His|Pro|Leu|Val|Ser|Gln| |
|495| | | |500| | | | |505| | | | |510| | |

| | | | | | | | | | | | | | | | | |
|---|---|---|---|---|---|---|---|---|---|---|---|---|---|---|---|---|
|gcc|atg|gtg|gtg|ggc|gat|ggt|aaa|cca|ttc|gtt|ggc|ctg|ctg|gtg|acc|1824|
|Ala|Met|Val|Val|Gly|Asp|Gly|Lys|Pro|Phe|Val|Gly|Leu|Leu|Val|Thr| |
| | | | |515| | | | |520| | | | |525| | |

| | | | | | | | | | | | | | | | | |
|---|---|---|---|---|---|---|---|---|---|---|---|---|---|---|---|---|
|ttg|gat|cca|gat|atg|ttg|aag|cgg|tgg|aag|ctg|aac|cac|aac|att|gcg|1872|
|Leu|Asp|Pro|Asp|Met|Leu|Lys|Arg|Trp|Lys|Leu|Asn|His|Asn|Ile|Ala| |
| | | |530| | | | |535| | | | |540| | | |

| | | | | | | | | | | | | | | | | |
|---|---|---|---|---|---|---|---|---|---|---|---|---|---|---|---|---|
|gaa|tcc|cgc|acg|gtt|tct|gag|att|gct|act|gat|cct|gca|ctg|cgt|gcg|1920|
|Glu|Ser|Arg|Thr|Val|Ser|Glu|Ile|Ala|Thr|Asp|Pro|Ala|Leu|Arg|Ala| |
| | |545| | | | |550| | | | |555| | | | |

| | | | | | | | | | | | | | | | | |
|---|---|---|---|---|---|---|---|---|---|---|---|---|---|---|---|---|
|gaa|atc|cag|gat|gca|gtc|aac|aac|gct|aat|gcc|acg|gtg|tct|cat|tca|1968|
|Glu|Ile|Gln|Asp|Ala|Val|Asn|Asn|Ala|Asn|Ala|Thr|Val|Ser|His|Ser| |
| |560| | | | |565| | | | |570| | | | | |

| | | | | | | | | | | | | | | | | |
|---|---|---|---|---|---|---|---|---|---|---|---|---|---|---|---|---|
|gag|gcg|atc|aag|cgg|ttc|tac|atc|ctt|gat|cgc|gac|ctg|acc|gag|gaa|2016|
|Glu|Ala|Ile|Lys|Arg|Phe|Tyr|Ile|Leu|Asp|Arg|Asp|Leu|Thr|Glu|Glu| |
|575| | | |580| | | | |585| | | | |590| | |

| | | | | | | | | | | | | | | | | |
|---|---|---|---|---|---|---|---|---|---|---|---|---|---|---|---|---|
|gcc|gac|gag|ctg|acc|cca|acg|ctg|aag|gtc|aag|cgc|aac|gtt|gtt|gtt|2064|
|Ala|Asp|Glu|Leu|Thr|Pro|Thr|Leu|Lys|Val|Lys|Arg|Asn|Val|Val|Val| |
| | | | |595| | | | |600| | | | |605| | |

| | | | | | | | | | | | | | |
|---|---|---|---|---|---|---|---|---|---|---|---|---|---|---|
|cgc|cgt|tac|gca|gac|gcc|atc|gac|cac|atc|tac|aac|cga|tgagtaacac| |2113|
|Arg|Arg|Tyr|Ala|Asp|Ala|Ile|Asp|His|Ile|Tyr|Asn|Arg| | | |
| | |610| | | | |615| | | | | | | | agagacccaa tttgattggg atggatcgac atggacccgc accgaagtcg gcgaagcacc     2173 aacacgcttc gctgtgggcg tgatggagga tttcgcctac attgcagcca ctggcacgga     2233 cggggatgaa gagttctta ctttgggctc aaatccgggt ctgacgtttg gtgatcccga      2293 gtggctt                                                              2300

<210> SEQ ID NO 2
<211> LENGTH: 619
<212> TYPE: PRT
<213> ORGANISM: Corynebacterium glutamicum

<400> SEQUENCE: 2

Leu Asn Leu Thr Met Thr Ser Pro Asn Thr Leu Gln Glu Tyr Thr Glu
1               5                   10                  15

Pro Ala Lys Tyr Thr Ile Gly Glu Ser Glu Thr Cys Leu Thr Ala Leu
            20                  25                  30

Leu Asp Gln Ile Lys Thr Arg Pro Tyr Gly Val Leu Phe Ser Lys Pro
        35                  40                  45

Ala Asn Tyr Glu Trp Val Asn Val Thr Ala Lys Glu Phe Gln Asp Glu
    50                  55                  60

Val Phe Ala Val Ala Lys Gly Ile Ile Ser Val Gly Val Glu Gln Gly
65                  70                  75                  80

-continued

```
Asp Arg Val Ala Leu Leu Ser Asn Thr Arg Tyr Glu Trp Ala Val Leu
                85                  90                  95

Asp Phe Ala Ile Trp Ala Ala Gly Ala Val Ser Val Pro Ile Tyr Ser
            100                 105                 110

Ser Ser Ser Leu Ser Gln Ile Glu Trp Ile Ile Glu Asp Ser Gly Ala
        115                 120                 125

Val Leu Ala Ile Thr Glu Thr Pro Asp His Thr Asp Leu Met Lys Asn
    130                 135                 140

Leu Val Ile Gly Glu Asp Gly Thr Pro Ala Ile Lys Gly Ser Pro Ser
145                 150                 155                 160

Lys Leu Arg Arg Ile Leu Glu Ile Asn Ser Ser Ala Leu Glu Thr Leu
                165                 170                 175

Lys Phe Glu Gly Arg Glu Leu Ser Asp Glu Leu Val Trp Glu Arg Ile
            180                 185                 190

His Ala Thr Lys Ala Ala Asp Leu Ala Ser Leu Val Tyr Thr Ser Gly
        195                 200                 205

Thr Thr Gly Arg Pro Lys Gly Cys Glu Leu Ser His Tyr His Trp Leu
    210                 215                 220

Ala Glu Val Arg Ala Leu Ile Thr Asn Asp Ile Gly Ala Ile Ala Met
225                 230                 235                 240

Pro Gly Ser Arg Leu Leu Thr Phe Leu Pro Leu Ala His Val Leu Ala
                245                 250                 255

Arg Ala Val His Leu Ala Phe Ala Val Thr Gly Ala Thr Gln Ser His
            260                 265                 270

Trp Ser Asp Phe Ser Thr Leu Thr Leu Glu Leu Gln Arg Ser Arg Pro
        275                 280                 285

Asn Leu Ile Leu Gly Val Pro Arg Val Phe Glu Lys Val Arg Asn Ala
    290                 295                 300

Ala Ala Ala Asn Ala Ala Asp Gly Gly Ala Ile Lys Arg Ile Met Phe
305                 310                 315                 320

Glu Arg Ala Glu Lys Ala Ala Ile Glu Tyr Ser Met Ala Leu Asp Thr
                325                 330                 335

Ala Glu Gly Pro Ser Lys Ser Gln Val Met Ala His Lys Ala Phe Asp
            340                 345                 350

Lys Leu Val Tyr Ser Lys Ile Arg Ala Ala Val Gly Gly Asp Val Gln
        355                 360                 365

Tyr Ala Ile Thr Gly Gly Ser Ala Met Gly Gln Glu Leu Leu His Phe
    370                 375                 380

Phe Arg Gly Val Gly Met Thr Ile Tyr Glu Gly Tyr Gly Leu Thr Glu
385                 390                 395                 400

Ser Ala Ala Ala Ala Val Asp Phe Thr Asp Gln Lys Ile Gly Thr
                405                 410                 415

Val Gly Lys Pro Met Gly Gly Met Thr Ile Lys Ile Asn Glu Asp Gly
            420                 425                 430

Glu Ile Met Leu Lys Gly Glu Met Leu Phe Gln Gly Tyr Trp Asn Asn
        435                 440                 445

Pro Glu Ala Thr Ala Glu Ala Leu His Asp Gly Trp Phe Asn Thr Gly
    450                 455                 460

Asp Leu Gly Glu Leu Leu Glu Ser Gly His Leu Val Ile Thr Gly Arg
465                 470                 475                 480

Lys Lys Asp Leu Ile Val Thr Ala Gly Gly Lys Asn Val Ser Pro Gly
                485                 490                 495

Pro Met Glu Asp Ile Ile Arg Ala His Pro Leu Val Ser Gln Ala Met
```

-continued

```
                    500                 505                 510
Val Val Gly Asp Gly Lys Pro Phe Val Gly Leu Leu Val Thr Leu Asp
            515                 520                 525

Pro Asp Met Leu Lys Arg Trp Lys Leu Asn His Asn Ile Ala Glu Ser
            530                 535                 540

Arg Thr Val Ser Glu Ile Ala Thr Asp Pro Ala Leu Arg Ala Glu Ile
545                 550                 555                 560

Gln Asp Ala Val Asn Asn Ala Asn Ala Thr Val Ser His Ser Glu Ala
                565                 570                 575

Ile Lys Arg Phe Tyr Ile Leu Asp Arg Asp Leu Thr Glu Glu Ala Asp
            580                 585                 590

Glu Leu Thr Pro Thr Leu Lys Val Lys Arg Asn Val Val Val Arg Arg
            595                 600                 605

Tyr Ala Asp Ala Ile Asp His Ile Tyr Asn Arg
            610                 615
```

<210> SEQ ID NO 3
<211> LENGTH: 24
<212> TYPE: DNA
<213> ORGANISM: Corynebacterium glutamicum

<400> SEQUENCE: 3
tgattggtgc agatataaga agtt                                      24

<210> SEQ ID NO 4
<211> LENGTH: 17
<212> TYPE: DNA
<213> ORGANISM: Corynebacterium glutamicum

<400> SEQUENCE: 4
cagcgaagcg tgttggt                                              17

FADD15 GENE OF *CORYNEBACTERIUM GLUTAMICUM*, ENCODING AN ACYL-COA SYNTHASE POLYPEPTIDE

RELATED APPLICATION DATA

This application is a Continuation-In-Part of U.S. patent application Ser. No. 09/577,848 filed May 25, 2000 now abandoned, which application claims priority under 35 U.S.C §119 from German Patent Appln. No. 10021831.8, filed in Germany on May 4, 2000. The above-identified U.S. patent application and German patent application are entirely incorporated herein by reference. The invention provides genetically modified coryneform bacteria, nucleotide sequences which code for acyl-CoA synthase and a method for the fermentative preparation of amino acids, in particular L-lysine, using coryneform bacteria in which the fadD15 gene, which codes for acyl-CoA synthase, is amplified. All references cited herein are expressly incorporated by reference. Incorporation by reference is also designated by the term "I.B.R." following any citation.

BACKGROUND ART

Amino acids, in particular L-lysine, are used in human medicine and in the pharmaceuticals industry, but in particular in animal nutrition.

It is known that amino acids are prepared by fermentation from strains of coryneform bacteria, in particular *Corynebacterium glutamicum*. Because of their great importance, work is constantly being undertaken to improve the preparation methods. Improvements to the methods can relate to fermentation measures, such as e.g. stirring and supply of oxygen, or the composition of the nutrient media, such as e.g. the sugar concentration during the fermentation, or the working up to the product form by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the lysine analogue S-(2-aminoethyl)-cysteine, or are auxotrophic for metabolites of regulatory importance and produce L-amino acids, such as e.g. L-lysine, are obtained in this manner.

Methods of the recombinant DNA technique have also been employed for some years for improving the strain of *Corynebacterium* strains which produce amino acids, by amplifying individual amino acid biosynthesis genes and investigating the effect on the amino acid production. Review articles in this context are to be found, inter alia, in Kinoshita ("Glutamic Acid Bacteria", in: Biology of Industrial Microorganisms, Demain and Solomon (Eds.) I.B.R., Benjamin Cummings, London, UK, 1985, 115–142 I.B.R.), Hilliger (BioTec 2, 40–44 (1991) I.B.R.), Eggeling (Amino Acids 6:261–272 (1994) I.B.R.), Jetten and Sinskey (Critical Reviews in Biotechnology 15, 73–103 (1995) I.B.R.) and Sahm et al. (Annuals of the New York Academy of Science 782, 25–39 (1996) I.B.R.).

OBJECT OF THE INVENTION

The object of the present invention was to provide new aids for improved fermentative preparation of amino acids, in particular L-lysine.

Amino acids, in particular L-lysine, are used in human medicine, in the pharmaceuticals industry and in particular in animal nutrition. There is therefore a general interest in providing new improved methods for the preparation of amino acids, in particular L-lysine.

When L-lysine or lysine are mentioned in the following, not only the base but also the salts, such as e.g. lysine monohydrochloride or lysine sulfate, are also meant by this.

SUMMARY OF THE INVENTION

The new DNA sequence of *C. glutamicum* which codes for the fadD15 gene and which as a constituent of the present invention is SEQ ID NO 1 and related sequences. The amino acid sequence of the corresponding gene product of the cma gene has furthermore been derived from the present DNA sequence. The resulting amino acid sequence of the fadD15 gene product is SEQ ID NO 2 and related sequences.

BRIEF DESCRIPTION OF THE DRAWINGS

The present invention will be further understood with reference to the drawing offered here for illustration only and not in limitation of this invention.

FIG. 1: Map of the plasmid pJC1fadD15

FIG. 2: Growth (OD 600 nm) of ATCC 13032 and ATCC 13032/pJC1fadD15 at 40° C.

DETAILED DESCRIPTION OF THE INVENTION

The invention provides a genetically modified coryneform bacterium, in which its fadD15 gene, which codes for acyl-CoA synthase, is amplified.

The term "amplification" in this connection describes the increase in intracellular activity of one or more enzymes in a microorganism which are coded by the corresponding DNA.

Amplification can be achieved with the aid of various manipulations of the bacterial cell.

To achieve an amplification, in particular an overexpression, the number of copies of the corresponding genes can be increased, a potent promoter can be used, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine or L-glutamate production. It is also possible to use a gene which codes for a corresponding enzyme with a high activity. The expression is likewise improved by measures to prolong the life of the m-RNA. Furthermore, the enzyme activity is also increased overall by preventing the degradation of the enzyme. These measures can optionally also be combined as desired.

The microorganisms which the present invention provides can prepare L-amino acids, in particular L-lysine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum*, are, for example, the known wild-type strains

*Corynebacterium glutamicum* ATCC13032
*Corynebacterium acetoglutamicum* ATCC15806
*Corynebacterium acetoacidophilum* ATCC13870

*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020
and L-lysine-producing mutants or strains prepared therefrom, such as, for example
*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715.

The present invention also provides an isolated polynucleotide from coryneform bacteria, comprising a polynucleotide sequence chosen from the group consisting of
a) polynucleotide which is homologous to the extent of at least 70% with a polynucleotide which codes for a polypeptide which comprises the amino acid sequence of SEQ ID No. 2,
b) polynucleotide which codes for a polypeptide which comprises an amino acid sequence which is homologous to the extent of at least 70% with the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c).

In the context of the present Application, a polynucleotide sequence is "homologous" to the sequence according to the invention if it coincides in its base composition and sequence with the sequence according to the invention to the extent of at least 70%, preferably at least 80%, particularly preferably at least 90%. According to the present invention, a "homologous protein" is to be understood as proteins which have an amino acid sequence which coincide with the amino acid sequence coded by the fadD15 gene (SEQ ID No. 1) to the extent of at least 70%, preferably at least 80%, particularly preferably at least 90%, "coincide" being understood as meaning that either the corresponding amino acids are identical or they are amino acids which are homologous to one another. Those amino acids which correspond in their properties, in particular in respect of charge, hydrophobicity, steric properties etc., are called "homologous amino acids".

The invention also provides a polynucleotide as described above, this preferably being a DNA which is capable of replication, comprising:
(i) the nucleotide sequence shown in SEQ ID No. 1, or
(ii) at least one sequence which corresponds to sequence (i) in the context of the degeneration of the genetic code, or
(iii) at least one sequence which hybridizes with the sequence complementary to sequence (i) or (ii), and optionally
(iv) mutations of neutral function in (i) which lead to the same or a homologous amino acid.

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R. Hybridization of complementary sequences can occur at varying degrees of stringency. Sambrook et al.: Molecular Cloning, A Laboratory Manual (Cold Spring Harbor Laboratory Press, 1989) I.B.R.

Hybridization of complementary sequences can occur at varying degrees of stringency. Sambrook et al.: Molecular Cloning, A Laboratory Manual (Cold Spring Harbor Laboratory Press, 1989) I.B.R. Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R.

Comprehensive descriptions can be found in known textbooks of genetics and molecular biology, such as e.g. that by Hagemann ("Allgemeine Genetik" [General Genetics], Gustav Fischer Verlag, Stuttgart, 1986) I.B.R.

Possible mutations are transitions, transversions, insertions and deletions. Depending on the effect of the amino acid exchange on the enzyme activity, missense mutations or nonsense mutations are referred to. Insertions or deletions of at least one base pair in a gene lead to frame shift mutations, as a consequence of which incorrect amino acids are incorporated or translation is interrupted prematurely. Deletions of several codons typically lead to a complete loss of the enzyme activity.

Instructions on generation of such mutations are prior art and can be found in known textbooks of genetics and molecular biology, such as e.g. the textbook by Knippers ("Molekulare Genetik" [Molecular Genetics], 6th edition, Georg Thieme Verlag, Stuttgart, Germany, 1995) I.B.R., that by Winnacker ("Gene und Klone" [Genes and Clones], VCH Verlagsgesellschaft, Weinheim, Germany, 1990) I.B.R. or that by Hagemann ("Allgemeine Genetik" [General Genetics], Gustav Fischer Verlag, Stuttgart, 1986) I.B.R.

The invention also provides a vector containing one of the stated polynucleotides and coryneform bacteria acting as host cell which contain the vector or in which the fadD15 gene is amplified.

The invention also provides
a polynucleotide which is capable of replication and comprises the nucleotide sequence SEQ ID No. 1, or consists of it,
a polynucleotide which codes for a polypeptide which comprises the amino acid sequence SEQ ID No. 2, or consists of it,
a vector containing the DNA sequence of *C. glutamicum* which codes for the fadD15 gene, contained in the vector pJC1fadD15, deposited in *Corynebacterium glutamicum* under number 13249,
and coryneform bacteria serving as the host cell, which contain the vector or in which the fadD15 gene is amplified.

The invention also provides polynucleotides which comprise the complete gene with the polynucleotide sequence corresponding to SEQ ID No. 1 or fragments thereof, and which are obtainable by screening by means of hybridization of a corresponding gene library with a probe which comprises the sequence of the polynucleotide mentioned, according to SEQ ID No. 1, or a fragment thereof, and isolation of the DNA sequence mentioned.

Polynucleotide sequences according to the invention are also suitable as hybridization probes for RNA, cDNA and DNA, in order to isolate, in the full length, cDNA which code for acyl-CoA synthase and to isolate those cDNA or genes which have a high similarity of with the sequence of the acyl-CoA synthase gene.

Polynucleotide sequences according to the invention are furthermore suitable as primers for the polymerase chain reaction (PCR), for the preparation of DNA which codes for acyl-CoA synthase.

Such oligonucleotides which serve as probes or primers can comprise more than 30, preferably up to 30, particularly preferably up to 20, especially preferably at lease 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" is understood as meaning peptides or proteins which comprise two or more amino acids bonded via peptide bonds.

The polypeptides according to the invention include a polypeptide according to SEQ ID No. 2, in particular those with the biological activity of the acyl carrier protein (acyl-CoA synthase), and also those which are homologous to the extent of at least 70% with the polypeptide according to SEQ ID No. 2, and preferably are homologous to the extent of at least 80% and in particular to the extent of at least 90% to 95% with the polypeptide according to SEQ ID No. 2, and have the activity mentioned.

The invention moreover provides a method for the fermentative preparation of amino acids, in particular L-lysine, using coryneform bacteria which in particular already produce an amino acid, and in which the nucleotide sequences which code for the fadD15 gene are amplified, in particular over-expressed.

The fadD15 gene, which codes for acyl-CoA synthase, (EC 6.2.1.3) of *C. glutamicum* is described for the first time in the present invention.

To isolate the fadD15 gene or also other genes of *C. glutamicum*, a gene library of this microorganism is first set up in *E. coli*. The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990 I.B.R.) or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495–508 (1987) I.B.R.). Bathe et al. (Molecular and General Genetics, 252:255–265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160–2164 I.B.R.) in the *E. coli* K-12 strain NM554 (Raleigh et al., 1988, Nucleic Acids Research 16:1563–1575 I.B.R.). Börmann et al. (Molecular Microbiology 6(3), 317-326)) (1992) I.B.R.) in turn describe a gene library of *C. glutamicum* ATCC13032 using the cosmid pHC79 (Hohn and Collins, Gene 11, 291–298 (1980) I.B.R.). To prepare a gene library of *C. glutamicum* in *E. coli* it is also possible to use plasmids such as pBR322 (Bolivar, Life Sciences, 25, 807–818 (1979) I.B.R.) or pUC9 (Vieira et al., 1982, Gene, 19:259–268 I.B.R.). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649 I.B.R.). The long DNA fragments cloned with the aid of cosmids can then in turn be subcloned and subsequently sequenced in the usual vectors which are suitable for sequencing, such as is described e.g. by Sanger et al. (Proceedings of the National Academy of Sciences of the United States of America, 74:5463–5467, 1977) I.B.R.

The new DNA sequence of *C. glutamicum* which codes for the fadD15 gene and which, as SEQ ID No. 1, is a constituent of the present invention, was obtained in this manner. The amino acid sequence of the corresponding protein has moreover been derived from the present DNA sequence by the methods described above. The resulting amino acid sequence of the fadD15 gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are moreover known among experts as "sense mutations" which do not lead to a fundamental change in the activity of the protein, i.e. are of neutral function. It is moreover known that changes on the N and/or C terminus of a protein cannot substantially impair the function thereof or can even stabilize this. Information in this context can be found by the expert, inter alia, in Ben-Bassat et al. (Journal of Bacteriology 169:751–757 (1987) I.B.R.), in O'Regan et al. (Gene 77:237–251 (1989) I.B.R.), in Sahin-Toth et al. (Protein Sciences 3:240–247 (1994) I.B.R.), in Hochuli et al. (Bio/Technology 6:1321–1325 (1988) I.B.R.) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID NO. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993 I.B.R.) and in Liebl et al. (International Journal of Systematic Bacteriology (1991) 41: 255–260 I.B.R.). Instructions for amplification of DNA sequences with the aid of the polymerase chain reaction (PCR) can be found by the expert, inter alia, in the handbook by Gait: Oligonukleotide synthesis: a practical approach (IRL Press, Oxford, UK, 1984) I.B.R. and in Newton and Graham: PCR (Spektrum Akademischer Verlag, Heidelberg, Germany, 1994) I.B.R.

In the work on the present invention, it has been found that coryneform bacteria produce amino acids, in particular L-lysine, in an improved manner after amplification of the fadD15 gene.

The genes or gene constructs under consideration can either be present in plasmids with a varying number of copies, or can be integrated and amplified in the chromosome. Alternatively, an over-expression of the genes in question can moreover be achieved by changing the composition of the media and the culture procedure.

Instructions in this context can be found by the expert, inter alia, in Martin et al. (Bio/Technology 5, 137–146 (1987) I.B.R.), in Guerrero et al. (Gene 138, 35–41 (1994) I.B.R.), Tsuchiya and Morinaga (Bio/Technology 6, 428–430 (1988) I.B.R.), in Eikmanns et al. (Gene 102, 93–98 (1991) I.B.R.), in European Patent Specification EPS 0 472 869 I.B.R., in U.S. Pat. No. 4,601,893 I.B.R., in Schwarzer and Pühler (Bio/Technology 9, 84–87 (1991) I.B.R., in Reinscheid et al. (Applied and Environmental Microbiology 60, 126–132 (1994) I.B.R.), in LaBarre et al. (Journal of Bacteriology 175, 1001–1007 (1993) I.B.R.), in Patent Application WO 96/15246 I.B.R., in Malumbres et al. (Gene 134, 15–24 (1993) I.B.R.), in Japanese Laid-Open Specification JP-A-10-229891 I.B.R., in Jensen and Hammer (Biotechnology and Bioengineering 58, 191–195 (1998) I.B.R.), in Makrides (Microbiological Reviews 60:512–538 (1996) I.B.R.) and in known textbooks of genetics and molecular biology.

By way of example, the fadD15 gene according to the invention was over-expressed with the aid of plasmids.

Suitable plasmids are those which are replicated and expressed in coryneform bacteria. Numerous known plasmid vectors, such as e.g. pZ1 (Menkel et al., Applied and Environmental Microbiology (1989) 64: 549–554 I.B.R.), pEKEx1 (Eikmanns et al., Gene 102:93–98 (1991) I.B.R.) or pHS2-1 (Sonnen et al., Gene 107:69–74 (1991) I.B.R.) are based on the cryptic plasmids pHM1519, pBL1 or pGA1. Other plasmid vectors, such as e.g. those based on pCG4 (U.S. Pat. No. 4,489,160 I.B.R.), or pNG2 (Serwold-Davis et al., FEMS Microbiology Letters 66, 119–124 (1990) I.B.R.), or pAG1 (U.S. Pat. No. 5,158,891 I.B.R.), can be used in the same manner.

An example of a plasmid, with the aid of which the fadD15 gene can be over-expressed is pJC1fadD15 (FIG. 1), which is based on the *E. coli—C. glutamicum* shuttle vector pJC1 (Cremer et al., 1990, Molecular and General Genetics 220: 478–480 I.B.R.) and contains the DNA sequence of *C. glutamicum* which codes for the fadD15 gene. It is contained in the strain DSM5715/pJC1fadD15.

Plasmid vectors which are moreover suitable are those with the aid of which the method of gene amplification by integration into the chromosome can be used, as has been described, for example, by Reinscheid et al. (Applied and Environmental Microbiology 60, 126–132 (1994) I.B.R.) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983) I.B.R.), pK18mob or pK19mob (Schäfer et al., Gene 145, 69–73 (1994) I.B.R.), pGEM-T (Promega corporation, Madison, Wis., USA), pCR2.1-TOPO (Shuman (1994 I.B.R.). Journal of Biological Chemistry 269:32678–84; U.S. Pat. No. 5,487, 993), pCR®Blunt (Invitrogen, Groningen, Holland; Bernard et al., Journal of Molecular Biology, 234: 534–541 (1993) I.B.R.) or pEM1 (Schrumpf et al, 1991, Journal of Bacteriology 173:4510–4516 I.B.R.). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994) I.B.R.). Methods for transformation are described, for example, by Thierbach et al. (Applied Microbiology and Biotechnology 29, 356–362 (1988) I.B.R.), Dunican and Shivnan (Bio/Technology 7, 1067–1070 (1989)) and Tauch et al. (FEMS Microbiological Letters 123, 343–347 (1994) I.B.R.). After homologous recombination by means of a "cross over" event, the resulting strain contains at least two copies of the gene in question.

In addition, it may be advantageous for the production of amino acids, in particular L-lysine, to amplify or over-express one or more enzymes of the particular biosynthesis pathway, of glycolysis, of anaplerosis, of the citric acid cycle or of amino acid export, in addition to the fadD15 gene.

Thus, for example, for the preparation of L-lysine, one or more genes chosen from the group consisting of the dapA gene which codes for dihydrodipicolinate synthase (EP-B 0 197 335 I.B.R.), or the dapE gene which codes for succinyl diaminopimelate desuccinylase, or the lysC gene which codes for a feed-back resistant aspartate kinase (Kalinowski et al. (1990), Molecular and General Genetics 224, 317–324 I.B.R.), or the gap gene which codes for glyceraldehyde-3-phosphate dehydrogenase (Eikmanns (1992), Journal of Bacteriology 174:6076–6086 I.B.R.), or the tpi gene which codes for triose phosphate isomerase (Eikmanns (1992), Journal of Bacteriology 174:6076–6086 I.B.R.), or the pgk gene which codes for 3-phosphoglycerate kinase (Eikmanns (1992), Journal of Bacteriology 174:6076–6086 I.B.R.), or the pyc gene which codes for pyruvate carboxylase (DE-A-19831609 I.B.R.), or the mqo gene which codes for malate-quinone oxidoreductase (Molenaar et al., European Journal of Biochemistry 254, 395–403 (1998) I.B.R.), or the lysE gene which codes for lysine export (DE-A-195 48 222 I.B.R.)

can be amplified, in particular over-expressed or amplified, at the same time.

In addition to amplification of the fadD15 gene it may moreover be advantageous for the production of amino acids, in particular L-lysine, to attenuate the pck gene which codes for phosphoenol pyruvate carboxykinase (DE 199 50 409.1, DSM 13047 I.B.R.) and/or the pgi gene which codes for glucose 6-phosphate isomerase (U.S. Ser. No. 09/396,478, DSM 12969 I.B.R.) and/or the poxB gene which codes for pyruvate oxidase (DE 1995 1975.7 I.B.R.)

at the same time.

In addition to over-expression of the fadD15 gene it may moreover be advantageous for the production of amino acids, in particular L-lysine, to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982 I.B.R.).

The microorganisms prepared according to the invention can be cultured continuously or discontinuously in the batch method (batch culture) or in the fed batch (feed method) or repeated fed batch method (repetitive feed method) for the purpose of production of amino acids, in particular L-lysine. A summary of known culture methods are described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991) I.B.R.) or in the textbook by Storhas (Bioreaktoren und periphere Einrichtungen [Bioreactors and Peripheral Equipment] (Vieweg Verlag, Braunschweig/Wiesbaden, 1994) I.B.R.).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R. Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must moreover comprise salts of metals, such as e.g. magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of lysine has formed. This target is usually reached within 10 hours to 160 hours.

The analysis of L-lysine can be carried out by anion exchange chromatography with subsequent ninhydrin derivatization, as described by Spackman et al. (Analytical Chemistry, 30, (1958), 1190) I.B.R.

The following microorganism has been deposited at the Deutsche Sammlung für Mikrorganismen und Zellkulturen (DSMZ=German Collection of Microorganisms and Cell Cultures, Braunschweig, Germany) in accordance with the Budapest Treaty:

Corynebacterium glutamicum strain DSM5715/pJC1fadD15 as DSM 13249

The method according to the invention is used for the fermentative preparation of amino acids, in particular L-lysine.

Legend To the Figures:

FIG. 1: Map of the plasmid pJC1fadD15

The abbreviations and designations used have the following meaning:

Orf2,rep: Plasmid-coded replication origin for *C. glutamicum* (of pHM1519)

fadD15: fadD15 (acyl-CoA synthase) gene from *C. glutamicum* ATCC13032

Kan: Kanamycin resistance gene

EcoRI: Cleavage site of the restriction enzyme EcoRI

NaeI: Cleavage site of the restriction enzyme NaeI

SphI: Cleavage site of the restriction enzyme SphI

SmaI: Cleavage site of the restriction enzyme SmaI

XmaI: Cleavage site of the restriction enzyme XmaI

ClaI: Cleavage site of the restriction enzyme ClaI

XhoI: Cleavage site of the restriction enzyme XhoI

NheI: Cleavage site of the restriction enzyme NheI

FIG. 2: Growth (OD 600 nm) of ATCC 13032 and ATCC 13032/pJC1fadD15 at 40° C.

OD: Optical density

EXAMPLES

The present invention is explained in more detail in the following with the aid of embodiment examples.

Example 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179 I.B.R.) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences USA 84:2160–2164 I.B.R.), obtained from Stratagene (La Jolla, USA, Product Description Super-Cos1 Cosmid Vektor Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC 13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extracts (Stratagene, La Jolla, USA, Product Description Gigapack II XL Packing Extract, Code no. 200217). For infection of the *E. coli* strain NM554 (Raleigh et al. 1988, Nucleic Acid Research 16:1563–1575 I.B.R.) the cells were taken up in 10 MM $MgSO_4$ and mixed with an aliquot of the phage suspension. The infection and titering of the cosmid library were carried out as described by Sambrook et al. (1989, Molecular Cloning: A laboratory Manual, Cold Spring Harbor I.B.R.), the cells being plated out on LB agar (Lennox, 1955, Virology, 1:190 I.B.R.) with 100 mg/l ampicillin. After incubation overnight at 37° C., recombinant individual clones were selected.

Example 2

Isolation and Sequencing of the fadD15 Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from Invitrogen (Groningen, Holland, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor I.B.R.), the DNA mixture being incubated overnight with T4 ligase (Pharmacia Biotech, Freiburg, Germany). This ligation mixture was then transformed by means of electroporation (Tauch et al. 1994, FEMS Microbiol Letters, 123:343–7 I.B.R.) into the $E.$ $coli$ strain DH5αMCR (Grant, 1990, Proceedings of the National Academy of Sciences U.S.A., 87:4645–4649 I.B.R.) and plated out on LB agar (Lennox, 1955, Virology, 1:190) with 50 mg/l zeocin. The plasmid preparation of the recombinant clones was carried out with Biorobot 9600 (Product No. 900200, Qiagen, Hilden, Germany). The sequencing was carried out by the dideoxy chain-stopping method of Sanger et al. (1977, Proceedings of the National Academy of Sciences U.S.A., 74:5463–5467 I.B.R.) with modifications according to Zimmermann et al. (1990, Nucleic Acids Research, 18:1067 I.B.R.). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then methoded using the Staden program package (1986, Nucleic Acids Research, 14:217–231 I.B.R.) version 97-0. The individual sequences of the pZero1 derivatives were assembled to a continuous contig. The computer-assisted coding region analysis was prepared with the XNIP program (Staden, 1986, Nucleic Acids Research, 14:217–231 I.B.R.). Further analyses were carried out with the "BLAST search programs" (Altschul et al., 1997, Nucleic Acids Research, 25:3389–3402 I.B.R.), against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 1857 base pairs, which was called the fadD15 gene. The fadD15 gene codes for a protein of 619 amino acids (SEQ ID No. 2).

Example 3

Cloning of the fadD15 Gene

Chromosomal DNA from $Corynebacterium$ $glutamicum$ ATCC 13032 was isolated as described by Tauch et al. (1995, Plasmid 33:168–179) I.B.R. A DNA fragment which carries the fadD15 gene was amplified with the aid of the polymerase chain reaction. The following primers were used for this:

(SEQ ID NO: 3) 5'-TGA TTG GTG CAG ATA TAA GAA GTT-3'

(SEQ ID NO: 4) 5'-CAG CGA AGC GTG TTG GT-3'

The primers shown were synthesized by MWG Biotech (Ebersberg, Germany) and the PCR reaction was carried out with them by the standard PCR method of Innis et al., (PCR protocol. A guide to methods and applications, 1990, Academic Press). The primers allow amplification of a DNA fragment of 2160 bp in size, which carries the fadD15 gene from $Corynebacterium$ $glutamicum.$ After separation by gel electrophoresis, the PCR fragment was isolated from the agarose gel with the QiaExII Gel Extraction Kit (Product No. 20021, Qiagen, Hilden, Germany).

The vector pUC18 (Norrander et al., Gene (26) 101–106 (1983) I.B.R.) was cleaved completely with the restriction endonuclease SmaI and dephosphorylated with shrimp alkaline phosphatase (Roche Diagnostics GmbH, Mannheim, Germany, Product Description SAP, Product No. 1758250).

The PCR fragment of approx. 2160 bp obtained in this manner was . . . with the prepared vector pUC18 and the batch was treated with T4 DNA ligase (Amersham Pharmacia, Freiburg, Germany, Product Description T4-DNA-Ligase, Code no.27-0870-04). The ligation batch was transformed in the $E.$ $coli$ strain DH5α (Hanahan, In: DNA cloning. A practical approach. Vol. I. IRL-Press, Oxford, Washington D.C., USA I.B.R.). Selection of plasmid-carrying cells was made by plating out the transformation batch on LB agar (Lennox, 1955, Virology, 1:190 I.B.R.) with 100 mg/l ampicillin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzyme EcoRI to check the plasmid by subsequent agarose gel electrophoresis. The resulting plasmid was called pUC18fadD15.

Example 4

Cloning of fadD15 in the Vector pJC1

The fadD15 gene was isolated from the plasmid pUC18fadD15 described in Example 3 by complete cleavage with the enzymes EcoRI and SalI. The fadD15 fragment 2201 bp in size was isolated from the agarose gel with the QiaExII Gel Extraction Kit (Product No. 20021, Qiagen, Hilden, Germany).

The $E.$ $coli$—$C.$ $glutamicum$ shuttle vector pJC1 (Cremer et al., 1990, Molecular and General Genetics 220: 478–80 I.B.R.) was used as the vector. This plasmid was cleaved completely with the restriction enzyme BamHI, treated with Klenow polymerase (Roche Diagnostics GmbH, Mannheim, Germany) and then dephosphorylated with shrimp alkaline phosphatase (Roche Diagnostics GmbH, Mannheim, Germany, Product Description SAP, Product No. 1758250).

The fadD15 fragment obtained in this manner was mixed with the prepared vector pJC1 and the batch was treated with T4 DNA ligase (Amersham Pharmacia, Freiburg, Germany, Product Description T4-DNA-Ligase, Code no.27-0870-04). The ligation batch was transformed in the $E.$ $coli$ strain DH5α (Hanahan, In: DNA cloning. A practical approach. Vol. I. IRL-Press, Oxford, Washington D.C., USA I.B.R.). Selection of plasmid-carrying cells was made by plating out the transformation batch on LB agar (Lennox, 1955, Virology, 1:190 I.B.R.) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzyme XbaI to check the plasmid by subsequent agarose gel electrophoresis. The resulting plasmid was called pJC1fadD15.

Example 5
Transformation of the Strain *C. glutamicum* DSM5715 with the Plasmid pJC1fadD15

The strain DSM5715 was transformed with the plasmid pJC1fadD15 using the electroporation method described by Liebl et al., (FEMS Microbiology Letters, 53:299–303 (1989) I.B.R.). Selection of the transformants took place on LBHIS agar comprising 18.5 g/l brain-heart infusion broth, 0.5M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology 144, 915–927 I.B.R.), cleaved with the restriction endonuclease XbaI, and the plasmid was checked by subsequent agarose gel electrophoresis. The resulting strain was called DSM5715/pJC1fadD15.

The following microorganism has been deposited at the Deutsche Sammlung fur Mikrorganismen und Zellkulturen (DSMZ=German Collection of Microorganisms and Cell Cultures, Braunschweig, Germany) in accordance with the Budapest Treaty:

*Corynebacterium glutamicum* DSM5715/pJC1fadD15 as DSM 13249

Example 6
Preparation of Lysine

The *C. glutamicum* strain DSM5715/pJC1fadD15 obtained in Example 5 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| (NH$_4$)$_2$SO$_4$ | 25 g/l |
| KH$_2$PO$_4$ | 0.1 g/l |
| MgSO$_4$ * 7H$_2$O | 1.0 g/l |
| CaCl$_2$ * 2H$_2$O | 10 mg/l |
| FeSO$_4$ * 7H$_2$O | 10 mg/l |
| MnSO$_4$ * H$_2$O | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| CaCO$_3$ | 25 g/l |

The CSL, MOPS and the salt solution were brought to pH 7 with aqueous ammonia and autoclaved. The sterile substrate and vitamin solutions were then added, as well as the CaCO$_3$ autoclaved in the dry state.

Culturing is carried out in a 10 ml volume in a 100 ml conical flask with baffles. Kanamycin (25 mg/l) was added. Culturing was carried out at 33° C. and 80% atmospheric humidity.

After 24 hours, the OD was determined at a measurement wavelength of 660 nm with a Biomek 1000 (Beckmann Instruments GmbH, Mutnchen). The amount of lysine formed was determined with an amino acid analyzer from Eppendorf-BioTronik (Hamburg, Germany) by ion exchange chromatography and post-column derivatization with ninhydrin detection.

The result of the experiment is shown in Table 1.

TABLE 1

| Strain | OD (660) | Lysine HCl g/l |
|---|---|---|
| DSM5715/pJC1fadD15 | 12.4 | 8.25 |
| DSM5715 | 11.9 | 7.8 |

Example 7
Improvement in the Growth Properties

The plasmid pJCfadD15 obtained in Example 4 was used for transformation of *C. glutamicum* strain ATCC 13032. This strain was transformed as described in Example 5 and investigated by restriction digestion and agarose gel electrophoresis as described in Example 5. The resulting strain ATCC 13032/pJCfadD15 was cultured in a nutrient medium suitable for determination of growth and the growth was determined at various temperatures.

For this, as described in Example 6, the strain was first incubated on an agar plate with the corresponding antibiotic (brain-heart agar with kanamycin (50 mg/l)) for 24 hours at 30° C. Starting from this agar plate culture, a preculture was seeded (10 ml medium in a 100 ml conical flask). The complete medium CgIII described in example 6 was used as the medium for the preculture. Kanamycin (25 mg/l) was added to this. The preculture was incubated for 16 hours at 30° C. at 240 rpm on a shaking machine. A main culture was seeded from this preculture such that the initial OD (600nm) of the main culture was 0.7. Medium MM was used for the main culture.

| Medium MM | |
|---|---|
| MOPS (morpholinopropanesulfonic acid) | 42 g/l |
| Glucose (autoclaved separately) | 40 g/l |
| (NH$_4$)$_2$SO$_4$ | 20 g/l |
| KH$_2$PO$_4$ | 1.0 g/l |
| K$_2$HPO$_4$ | 1.0 g/l |
| MgSO$_4$ * 7H$_2$O | 0.25 g/l |
| CaCl$_2$ * 2H$_2$O | 10 mg/l |
| FeSO$_4$ * 7H$_2$O | 10 mg/l |
| MnSO$_4$ * H$_2$O | 10 mg/l |
| ZnSO$_4$ * H$_2$O | 1 mg/l |

-continued

Medium MM

| | |
|---|---|
| CuSO₄ | 0.2 mg/l |
| NiCl₂ * 6H₂O | 0.02 mg/l |
| Biotin (sterile-filtered) | 0.2 mg/l |
| Protocatechuic acid (sterile-filtered) | 30 mg/l |

The MOPS and the salt solution were brought to pH 7 with aqueous ammonia and autoclaved. The sterile substrate and vitamin solutions were then added.

Culturing was carried out in a 60 ml volume in a 500 ml conical flask with baffles. Kanamycin (25 mg/l) was added. Culturing was carried out at 40° C. The OD was determined at a measurement wavelength of 600 nm with the Ultrospec 3000 (Pharmacia Biotech, Upsala, Sweden). The result of the experiment is shown in FIG. 2.

What is claimed is:

1. A bacterium transformed with an isolated polynucleotide which encodes an acyl-CoA synthase comprising the amino acid sequence of SEQ ID NO: y 2.

2. The bacterium of claim 1, wherein said bacterium is a coryneform bacterium selected from the group consisting of *Corynebacterium glutamicum, Corynebacterium acetoglutamicum, Corynebacterium acetoacidophilum, Corynebacterium thermoaminogenes, Corynebacterium melassecola, Brevibacterium flavum, Brevibacterium lactofermentum* and *Brevibacterium divaricatum* or from the species *Escherichia coli*.

3. The bacterium of claim 1, wherein said acyl-CoA synthase encoded by said isolated polynucleotide is overexpressed, and wherein said overexpression is achieved by increasing the number of copies of said isolated polynucleotide by transformation of said bacterium with a vector which comprises said isolated polynucleotide.

4. The bacterium of claim 3, wherein said isolated polynucleotide coding for said acyl-CoA synthase is comprised in a plasmid vector.

5. The bacterium of claim 4, wherein said plasmid vector is pJC1fad15 contained in the *Corynebacterium glutamicum* deposited under DSM 13249.

6. An isolated polynucleotide comprising a polynucleotide which encodes an acyl-CoA synthase comprising the amino acid sequence of SEQ ID NO: 2.

7. The polynucleotide of claim 6, wherein said polynucleotide is a recombinant DNA which is capable of replication in coryneform bacteria.

8. The polynucleotide of claim 6, wherein said polynucleotide is an RNA.

9. An isolated polynucleotide, consisting of SEQ ID NO: 1 or a fragment thereof which encodes an acyl-CoA synthase.

10. The isolated polynucleotide of claim 9, wherein said acyl-CoA synthase consists of the amino acid sequence of SEQ ID NO: 2.

11. An isolated polynucleotide fragment of SEQ ID NO: 1 or of the complete complement of SEQ ID NO: 1 consisting of at least 15 consecutive nucleotides.

12. An isolated polynucleotide comprising the complete complement of SEQ ID NO: 1.

13. A vector comprising the isolated polynucleotide of claim 6.

14. The vector according to claim 13, wherein said vector is pJC1fad15 contained in the host cell deposited under DSM 13249.

15. A vector comprising the isolated polynucleotide of claim 12.

16. A vector comprising the isolated polynucleotide of claim 9.

17. An isolated polynucleotide, comprising nucleotides 247 to 2103 of SEQ ID NO: 1which encodes an acyl-CoA synthase having the amino acid sequence of SEQ ID NO: 2.

* * * * *